(12) United States Patent
Grimm

(10) Patent No.: US 6,450,939 B1
(45) Date of Patent: Sep. 17, 2002

(54) HINGED SPACER ELEMENT FOR JOINING RADIOACTIVE SEEDS USED IN TREATMENT OF CANCER

(76) Inventor: Peter D. Grimm, 1211 E. Newton, Seattle, WA (US) 98102

(*) Notice: Subject to any disclaimer, the term of this patent is extended or adjusted under 35 U.S.C. 154(b) by 87 days.

(21) Appl. No.: 09/707,622

(22) Filed: Nov. 6, 2000

(51) Int. Cl.[7] .................................................. A61N 5/00
(52) U.S. Cl. ..................................... 600/8; 604/164.01
(58) Field of Search ...................... 600/7, 8; 604/93.01, 604/164.01

(56) References Cited

U.S. PATENT DOCUMENTS

| | | | |
|---|---|---|---|
| 4,784,116 A | * 11/1988 | Russell, Jr. et al. | 600/8 |
| 4,815,449 A | * 3/1989 | Horowitz | 600/7 |
| 5,242,373 A | * 9/1993 | Scott et al. | 600/7 |
| 5,860,909 A | * 1/1999 | Mick | 600/7 |
| 5,928,130 A | * 7/1999 | Schmidt | 600/7 |
| 6,095,967 A | * 8/2000 | Black et al. | 600/7 |
| 6,159,143 A | * 12/2000 | Lennox | 600/4 |
| 6,200,258 B1 | * 3/2001 | Slater et al. | 600/8 |
| 6,221,003 B1 | * 4/2001 | Sierocuk et al. | 600/7 |
| 6,228,049 B1 | * 5/2001 | Schroeder et al. | 604/93.01 |
| 6,264,600 B1 | * 7/2001 | Grimm | 600/7 |
| 6,273,851 B1 | * 8/2001 | Slater et al. | 600/8 |
| 2002/0049411 A1 | * 4/2002 | Lamoureux et al. | 604/164.01 |

* cited by examiner

*Primary Examiner*—Teresa Walberg
*Assistant Examiner*—Leonid Fastovsky
(74) *Attorney, Agent, or Firm*—Jensen & Puntigam, P.S.

(57) ABSTRACT

The spacer element (10) includes a central portion (16) and two end portions (18, 20). The spacer element is generally cylindrical in configuration and the two end sections are adapted to receive and hold a portion of radioactive seed elements (12, 14). The spacer element comprises two half-portions (22, 24) joined by a hinge element (26) positioned along a longitudinal edge of the spacer element. The two half-portions rotate about the longitudinal hinge element, moving from an open position, in which the radioactive seeds can be loaded by an operator into the spacer element, to a closed position, in which the radioactive seeds are held in the spacer element. A plurality of seeds and spacers can thus be conveniently assembled into a series string thereof for loading into a needle and subsequent insertion into the prostate.

8 Claims, 3 Drawing Sheets

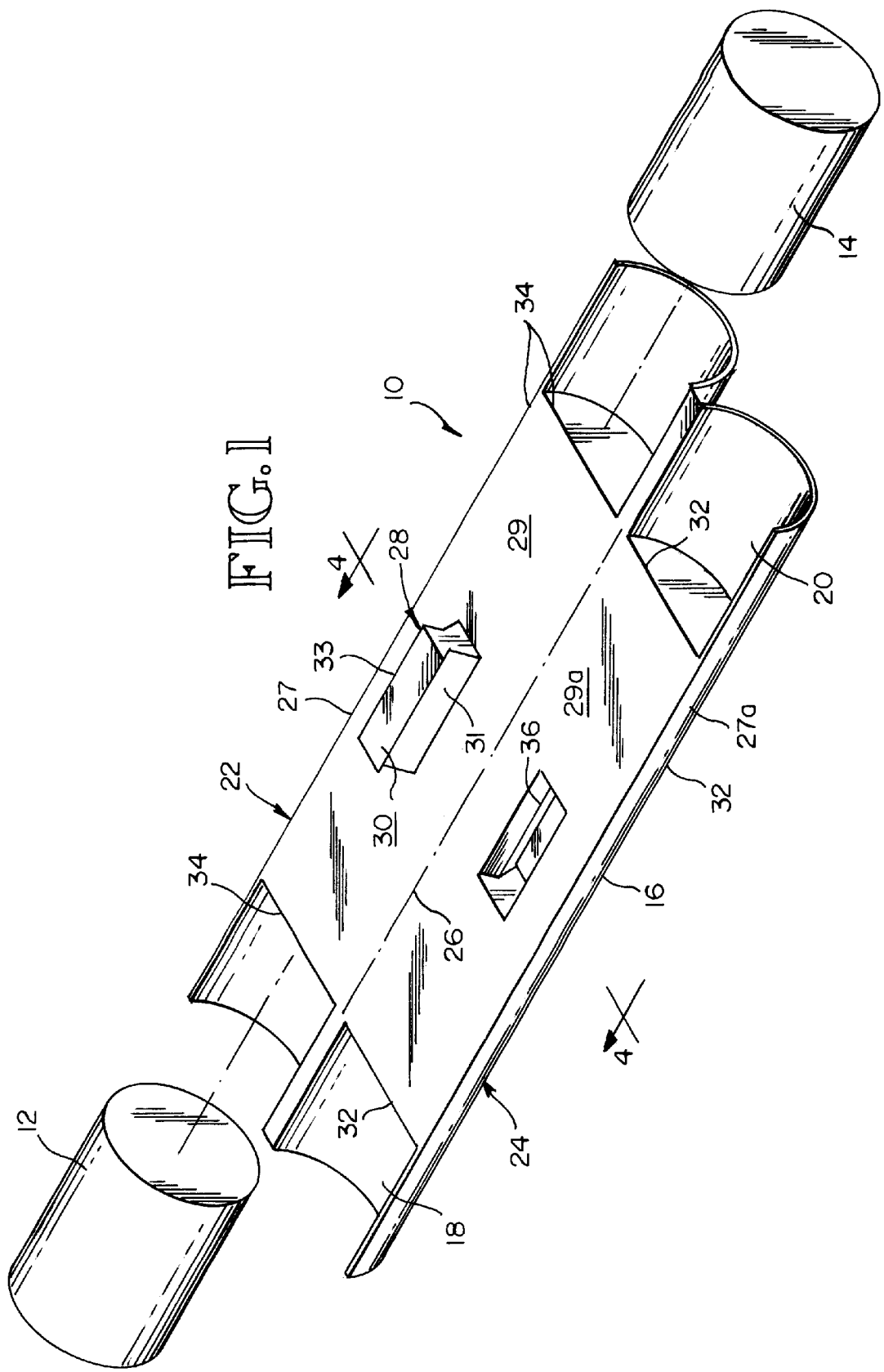

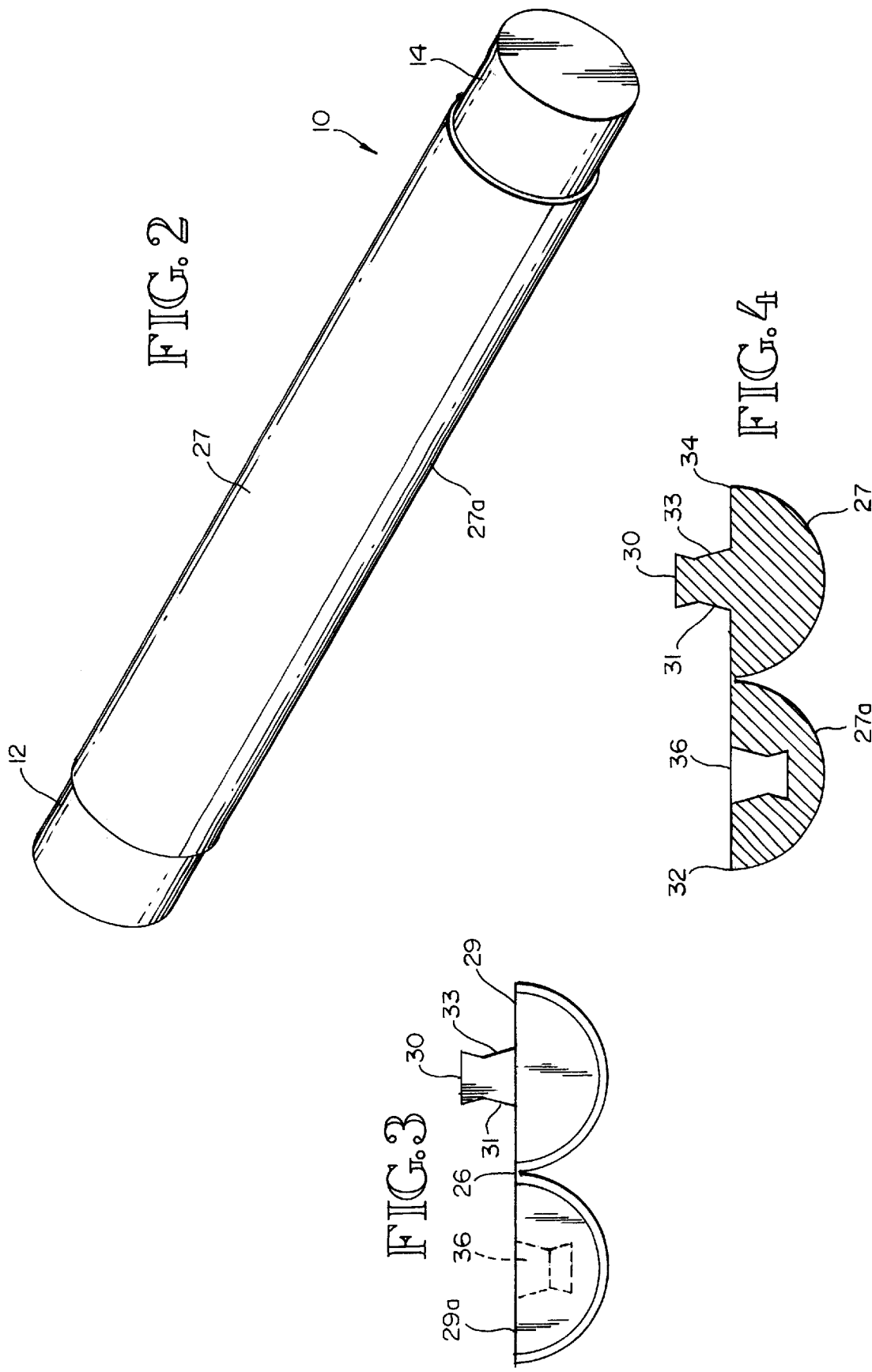

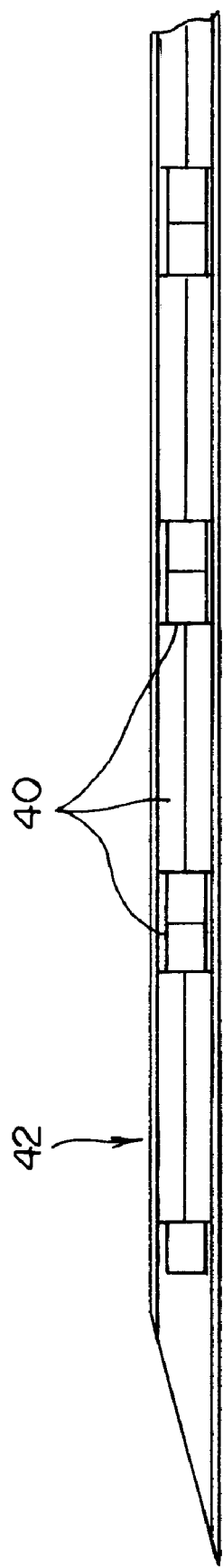

HINGED SPACER ELEMENT FOR JOINING RADIOACTIVE SEEDS USED IN TREATMENT OF CANCER

TECHNICAL FIELD

This invention relates generally to radioactive seed implant treatment for prostate cancer, and more specifically concerns a spacer element which is positioned between successive radioactive seeds in a radioactive seed string used in the treatment.

BACKGROUND OF THE INVENTION

A technique known as transperineal seed implantation, or brachytherapy, has been developed for delivering radioactive seeds to the prostate for treatment of cancer therein. In this technique, a plurality of elongated, hollow needles, each loaded with a series string of radioactive seeds, separated by spacer elements, are inserted into the prostate of the patient.

The loaded needles are accurately positioned within the prostate using ultrasound and a stepper apparatus, in accordance with a pre-planned dosimetry pattern. The needles are then removed, leaving the seeds and spacer string in place in the prostate. This technique, which has been quite successful, is described in more detail in U.S. Pat. No. 6,010,446, by the same inventor as in this application, the contents of which are hereby incorporated by reference.

In the brachytherapy technique, the spacer elements positioned between the successive radioactive seeds play an important role in maintaining the relative position of the radioactive seeds in the series string thereof, both within the needle during insertion and within the prostate after the needle has been removed. The spacer element shown in the '446 patent maintains the relative relationship between the seeds in the prostate and thus prevents them from migrating within the prostate. While the '446 spacer element was and is a significant advance over previous spacing arrangements, it is desirable to make the spacer element more user-friendly, i.e. easier to load the seeds therein. It is advantageous to make the process of joining successive radioactive seeds with spacer elements together in a series string of seeds and elements as easy and as fast as possible.

DISCLOSURE OF THE INVENTION

Accordingly, the present invention is a spacer element which is used with radioactive seeds to form a series string thereof, for needle implant treatment of prostate cancer. The spacer element comprises: a spacer element having a central section and two end sections which extend outwardly from the central section, the spacer element comprising two separate portions which are joined by a longitudinal hinge element, such that the two portions come adjacent one another when the spacer element is in a closed position and move apart from one another about the hinge element when the spacer element is moved into an open position, wherein the two end sections are each configured and adapted in such a manner, respectively, to receive and hold a portion of a radioactive seed when the spacer element is in its closed position and to permit convenient loading of radioactive seeds into the respective end sections when the spacer element is in its open position, which thereby permits convenient assembly of a series string of radioactive seeds and spacers; and wherein said string of spacer elements and radioactive seeds is readily fittable within a hollow needle for subsequent insertion into the prostate for use in radioactive seed therapy treatment.

BRIEF DESCRIPTION OF THE DRAWINGS

FIG. 1 is a perspective view of the spacer element of the present invention, showing the spacer element in its "open" position with the two adjoining radioactive seeds shown slightly exploded away from the spacer element.

FIG. 2 is a perspective view of the spacer element of FIG. 1, with the spacer element in its "closed" position and the radioactive seeds shown captured by the spacer element.

FIG. 3 is an end elevational view of the spacer element of FIG. 1, with the spacer element in its open position.

FIG. 4 is a lateral cross-sectional view of the spacer element of FIG. 1, taken along lines 4—4 in FIG. 1.

FIG. 5 is an elevational view showing a plurality of successive radioactive seeds and spacer elements in a needle used for treatment of cancer.

BEST MODE FOR CARRYING OUT THE INVENTION

FIGS. 1–4 show one embodiment of the spacer element of the present invention. The spacer element, shown generally at 10, is illustrated in conjunction with two separate radioactive seeds 12 and 14, which are linked together by the spacer element 10 as part of a seed/spacer string. The radioactive seeds 12 and 14 can be made from a variety of radioactive substances effective for treatment of cancer, but for prostate cancer, the radioactive substances will typically be Iodine-125 or Palladium-103. It should be understood, however, that seeds 12, 14 are shown to illustrate the spacing function of element 10 and are not a part of the present invention. The seeds can be any type of radioactive seed, either presently known or developed in the future, useful for cancer treatment or other medical or even non-medical use.

Spacer element 10 is typically made from material which is absorbable in living tissue. The overall spacer itself is rigid in the embodiment shown, although it could be flexible and therefore capable of bending to some extent. Examples of such material include vicryl absorbable suture material or similar material.

The spacer element 10 includes a central portion 16, which provides the actual physical spacing between the two seeds 12 and 14, and two end portions 18 and 20 which extend from the central portion 16 and are adapted and arranged to hold the radioactive seeds 12 and 14 therein. In the embodiment shown, spacer element 10 comprises two semi-cylindrical half-portions 22 and 24 joined along the lengths thereof by a longitudinal hinge element 26. Hinge element 26 can take a variety of configurations, including conventional hinge designs or other arrangements, such as a single or multiple flexible straps or two edge connected elements which are interleaved to provide a rotational capability.

Functionally, hinge element 26 must permit a rotation or movement of one half-portion of the element relative to the other. While the embodiment shown discloses half-portions 22 and 24, it should be understood that the portions could vary such that one portion has a larger volume than the other, such as one-third/two-thirds, etc. When the two portions are joined together, however, a whole, i.e. complete, spacer element results, as shown in the drawings.

In the embodiment shown, spacer element 10 is cylindrical, approximately 58 mm in length, with a diameter of approximately 1.6 mm. The end portions 18 and 20, which each receive and hold a portion of a radioactive seed, are 1.5 mm long in the embodiment shown. It should be understood, however, that these dimensions can be changed, depending upon the particular application and the dimensions of the seeds and the insertion needle.

Again, in the embodiment shown, the two end portions 18 and 20, when the spacer element is closed, each define a hollow, cup-like member to receive a radioactive seed. Typically, the walls of the end portions will be of a thickness which permits standard seeds to be securely held but will permit the spacer element to be placed within standard needles. The central portion of the spacer element will typically be solid. The central part of the half portions, respectively, includes a curved (semicircular in the embodiment shown) outer surface 27, 27a and a flat inner surface 29, 29a. The inner surfaces 29, 29a of the two half portions come adjacent each other when the spacer element is closed.

On flat surface 29 of one half-portion 22 will be a male joining element 28. In the embodiment shown, male element 28 is positioned approximately central of surface 29 of half-portion 22, and is approximately 2 mm long, 1 mm wide and 2 mm high. These dimensions can be varied. The top surface 30 of male element 28 is flat, with the longitudinal sides 31, 33 having an indentation, as shown in FIG. 4. The male element 28 is adapted to fit snugly within a mating female opening 36 in the flat surface 29a of the other half-portion 24. The longitudinal sides of the female receiving portion 36 each include an extending part which is designed to match the configuration of the corresponding indented side portions of male element 28. The combination of the male element 28 and female opening 36 provides a locking capability for the two hinged portions of the spacer element. When the spacer embodiment shown is in its closed position, the inner surfaces 29 and 29a, respectively, come adjacent one another, even touching one another, to produce in effect a single, unitary spacer element.

As indicated above, hinge element 26 can have a variety of configurations so that the two half portions of the spacer element can be brought together conveniently and completely. When the inner surfaces 29 and 29a of half-portions 22 and 24 come adjacent each other when the spacer element is in its closed position, the free longitudinal edges 34—34 of one half-portion thereof are adjacent with and in registry with the free longitudinal edges 32—32 of the other half-portion.

While the male element and female opening of the half-portions 22 and 24 do provide a desired locking capability for the spacer element, such a locking capability is not necessary to the invention. Hence, surfaces 29 and 29a can be completely flat.

In use, a plurality of alternating spacer elements and radioactive seeds are positioned in a series string for loading into a needle. The number of spacer elements and radioactive seeds will vary, depending upon the particular location in the prostate for the seed/spacer string and the dosimetry pattern. The spacer elements and seeds are initially positioned with the spacer elements in the "open" position. Radioactive seeds are then positioned in the end portions of each spacer element; when this is completed, the spacer elements are closed, forming an essentially unitary string of spacer elements and radioactive seeds. This seed/spacer string, shown generally at 40 in FIG. 5 is then loaded into a treatment needle 42.

The loaded needle is used in the treatment program described above. Briefly, after the loaded needle is inserted into the prostate in the specified position, through use of a template/stepper insertion apparatus, the needle is withdrawn in such a manner as to leave the string of radioactive seeds and spacer elements in place within the prostate. The spacer elements, which physically link successive radioactive seeds, will substantially prevent any migration of the individual seeds within the prostate, even with tissue movement within the prostate. The desired dosimetry pattern is thus maintained over time within the prostrate. The spacer element of the present invention, with its hinged, "clam shell-like" configuration, is easier for the technician to use to construct the seed spacer string.

Although a preferred embodiment of the invention has been disclosed here for purposes of illustration, it should be understood that various changes, modifications and substitutions may be incorporated without departing from the spirit of the invention, which is defined by the claims which follow.

What is claimed is:

1. A spacer element for use with radioactive seeds in needle implant treatment of prostate cancer, comprising:

a spacer element having a central section and two end sections extending outwardly therefrom, the spacer element comprising two separate portions joined by a longitudinal hinge element, such that the two portions come adjacent one another in a closed position of the spacer element and move apart from one another about the hinge element into an open position, wherein the two end sections are each configured and adapted, respectively, to receive and hold a portion of a radioactive seed when the spacer element is in its closed position and to permit convenient loading of radioactive seeds into the respective end sections when the spacer element is in its open position, thereby permitting convenient assembly of a series string of radioactive seeds and spacers; and wherein said string of spacer elements and radioactive seeds is fittable within a hollow needle for subsequent insertion into the prostate for use in radioactive seed therapy treatment.

2. The spacer element of claim 1, wherein the spacer element is flexible.

3. The spacer element of claim 1, wherein the hinge element extends the entire length of the spacer element.

4. The spacer element of claim 1, wherein the two portions are half-portions, substantially identical to each other.

5. The spacer element of claim 1, wherein the hinge element extends along one longitudinal edge of the spacer element.

6. The spacer element of claim 4, wherein the end sections of each portion are substantially semicircular and wherein the free longitudinal edges thereof come adjacent one another when the spacer element is in its closed position.

7. The spacer element of claim 1, wherein the central section includes a locking member in one portion and a receiving part in the other portion, wherein the locking member and the receiving member mate together in such a fashion that when the spacer element is in its closed position, the two portions are locked together.

8. The spacer element of claim 1, wherein the end sections are configured so that when the spacer element is in its closed position, the end sections securely hold a radioactive seed therein.

\* \* \* \* \*